United States Patent [19]

Hosoda

[11] 4,352,150
[45] Sep. 28, 1982

[54] LIGHT SOURCE DEVICE

[75] Inventor: Seiichi Hosoda, Fuchu, Japan

[73] Assignee: Olympus Optical Co. Ltd., Tokyo, Japan

[21] Appl. No.: 186,478

[22] Filed: Sep. 12, 1980

[30] Foreign Application Priority Data

Sep. 17, 1979 [JP] Japan .......................... 54-128386[U]

[51] Int. Cl.³ .............................................. F21V 7/00
[52] U.S. Cl. .................... 362/282; 362/217; 362/296; 362/362; 362/368; 362/263
[58] Field of Search ............... 362/217, 282, 296, 362, 362/368, 263

[56] References Cited

U.S. PATENT DOCUMENTS

| | | | |
|---|---|---|---|
| 2,739,228 | 3/1956 | Robins | 240/41.3 |
| 2,863,989 | 12/1958 | Wrigglesworth | 240/41.3 |
| 3,423,089 | 1/1969 | Andis | 362/263 |
| 3,702,395 | 11/1972 | Rosendahl | 362/282 |
| 4,053,756 | 10/1977 | Takahashi | 362/32 |
| 4,266,534 | 5/1981 | Ogawa | 362/32 |

FOREIGN PATENT DOCUMENTS

| | | | |
|---|---|---|---|
| 151130 | 10/1937 | Austria | 240/41.3 |
| 2318769 | 10/1973 | Fed. Rep. of Germany | 240/41.3 |
| 2658700 | 7/1977 | Fed. Rep. of Germany | 240/41.3 |

Primary Examiner—Stephen J. Lechert, Jr.

[57] ABSTRACT

A light source device comprises a light source lamp detachably fitted to a light source lamp rest mounted on a housing; and a reflection mirror-retracting mechanism comprising a swing member on which a reflection mirror is carried, and which swings between a first position in which the swing member causes the reflection mirror to face one end of the light source lamp and a second position in which the swing member retracts the reflection mirror from one end of the light source lamp, and fixing member for locking the swing member in the first position. The arrangement allows for the fitting, removal or replacement of the light source lamp without releasing the reflection mirror from its place each time.

12 Claims, 3 Drawing Figures

TO ENDOSCOPE

LIGHT SOURCE DEVICE

This invention relates to a light source device and more particularly to a light source device for an endoscope.

With a light source device for an endoscope, it is desired to set an electric flash tube used as a light source as close to a reflection mirror as possible in order to elevate the efficiency of reflecting light rays.

The conventional endoscope light source device is not provided with means for relatively spacing an electric flash tube and reflection mirror from each other. These light source components are fixed to a housing or any other member. Therefore, the reflection mirror has to be removed with troublesome work, before the flash tube is set in place, taken off or replaced. Thereafter the reflection mirror has to be set in place again. Consequently, the known endoscope light source device has been regarded as extremely inconvenient.

The object of this invention is to provide an endoscope light source device fitted with a reflection mirror-retracting mechanism which removes a reflection mirror from its normal place near a light source lamp to let the light source lamp be easily fitted, taken off or replaced, and after the fitting, removal or replacement of the light source lamp, again immovably fixes the reflection mirror in a position close to the light source lamp.

An endoscope light source device embodying this invention comprises a housing, a light source lamp detachably fitted to a lamp rest mounted on the outer wall of the housing, a reflection mirror, a reflection mirror-retracting mechanism which is set adjacent to one end of the light source lamp. The retracting mechanism comprises a swing member and fixing means. The swing member carries the reflection mirror and swings around one end of the swing member between a first position in the reflection mirror is brought adjacent to one end of the light source lamp and a second position in which the reflection mirror is retracted from the light source lamp. The fixing means is used for locking the swing member in the first position.

This invention can be fully understood from the following detailed description with reference to the accompanying drawings, in which.

Figure 1:
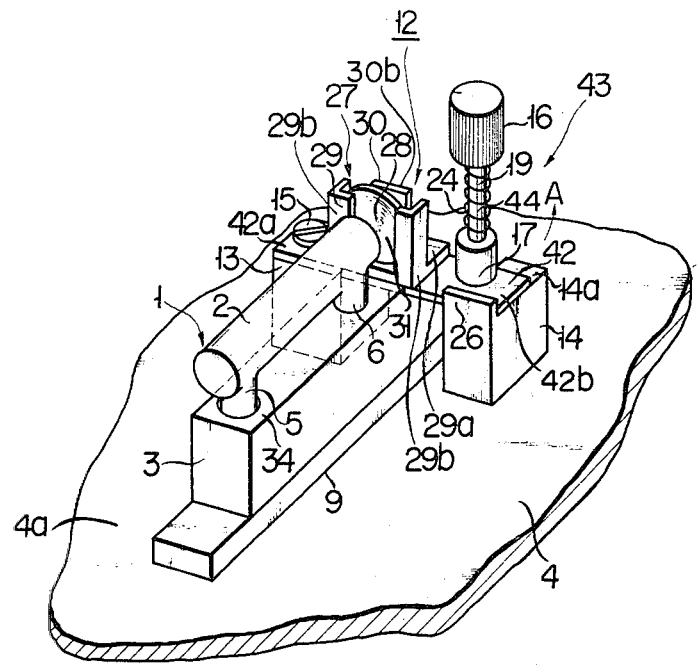
FIG. 1 is a perspective view of an endoscope light source device embodying this invention.
Figure 2:
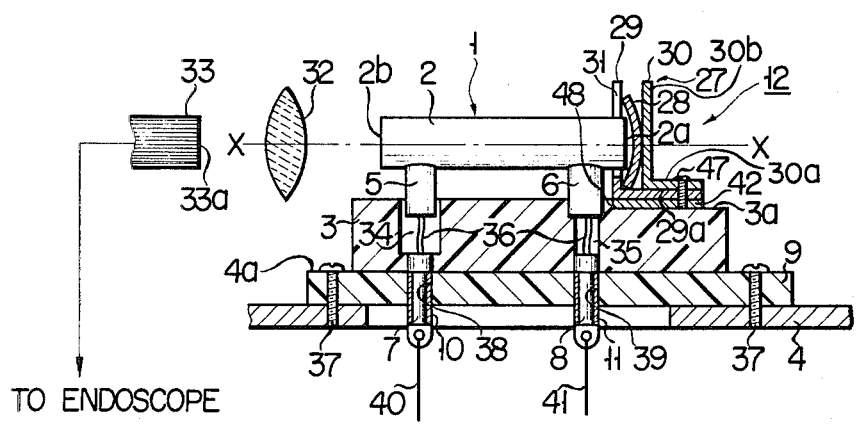
FIG. 2 is a longitudinal cross sectional view of an arrangement by which the light source device of FIG. 1 and reflection mirror are set in place.

Referring to FIGS. 1 and 2, an endoscope light source device comprises a light source lamp 1 formed of an electric flash tube 2 such as a stroboscopic lamp and a parallelepiped base 3 prepared from an electric insulating material such as ceramics. A pair of parallel cylindrical electrode sections 5, 6 project in the same direction from the respective end portion of the lateral wall of the electric flash tube 2. The electrode section 5 is loosely fitted into a round hole 34 formed in the base 3. The electrode section 6 is fitted into a round hole 35 similarly formed in the base 3 such that the electric flash tube 2 is supported on the base 3 in a state saved from breakage resulting from thermal expansion. Pins 7, 8 concentric with the round holes 34, 35 project from the remote side of the base 3 from that on which the electric flash tube 2 is supported. The pins 7, 8 are electrically connected to electrodes (not shown) in the electrode sections 5, 6 by means of flexible electric conductive wire pieces 36.

A narrow plate-shaped light source lamp rest 9 prepared from electric insulating material such as ceramics is mounted on the outer surface 4a of the housing 4 of the endoscope light source device by means of, for example, screws 37. Hollow receptacles 10, 11 are received in penetrating holes 38, 39 alignable with the pins 7, 8. These pins 7, 8 are inserted into the hollow receptacles 10, 11. The lower ends of the pins 7, 8 are coupled to leads 40, 41 connected to a D.C. source (not shown).

A reflection mirror-retracting mechanism denoted by the general reference numeral 12 is disposed at one end 2a of the electric flash tube 2, and comprises a pair of parallelepiped supports 13, 14 mounted on the outer surface 4a of the housing 4 on both sides of the base 3 and a narrow metal plate swing member 42 extending across the surface 3a of the base 3 in close contact therewith. As shown in FIG. 1, one end portion 42a of the swing member 42 is mounted on the support 13, for example, by an externally threaded pivotal shaft 15 in a state horizontally swingable in parallel with the outer surface 4a of the housing 4. The other end portion 42b of the swing member 42 contacts the upper surface of the other support 14.

Figure 3:
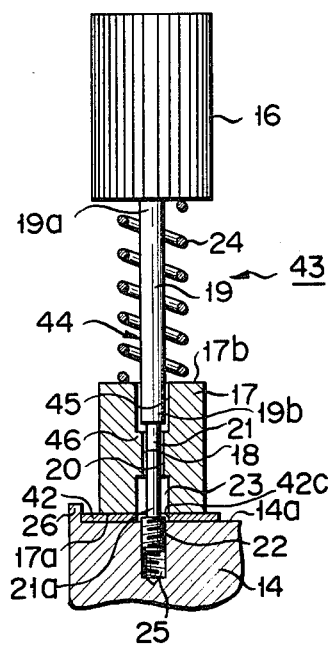
FIG. 3 is a longitudinal sectional view of the fixing means of FIG. 1.

Referring to FIGS. 1 and 3, the other end portion 42b of the swing member 42 is provided with swing member fixing means 43. This swing member fixing means 43 comprises a ring-shaped guide member 17, which has a concentric penetrating guide hole 18 and the lower end 17a of which is fixed to the other end portion 42b of the swing member 42, and a rod 44 extending through the penetrating hole 18. One end of the rod 44 is fitted into an engagement hole 25 formed in the upper surface of the support 14.

With the embodiment of FIGS. 1 and 3, the rod 44 comprises a cylindrical trunk section 19, one end 19a of which is fitted with a larger diameter cylindrical knob 16; a cylindrical sliding section 21 which extends concentrically from the other end 19b of the trunk section 19 and has a smaller outer diameter than the trunk section 19; and a cylindrical engagement section 22 which concentrically extends from the lower end 21a of the sliding member 21 and has substantially the same outer diameter as the trunk section 19. The engagement section 22 is provided with external threads. The engagement hole 25 is provided with internal threads complementarily shaped to the external threads. Thus, the engagement section 22 and engagement hole 25 can be threadedly engaged with each other.

The guide hole 18 of the guide member 17 comprises three concentric cylindrical hole sections: an intermediate hole section 20 whose inner diameter is substantially equal to the outer diameter of the sliding section 21 of the rod 44 and which is shorter than the sliding member 21; a first cylindrical hole end section 23 which extends from that end of the intermediate hole section 20 which is near the swing member 42 to the lower end 17a of the guide member 17 and further passes through the other end portion 42b of the swing member 42 (that is, a penetrating hole 26a is formed in the other end portion 42c), and whose inner diameter is equal to or larger than the outer diameter of the engagement section 22 of the rod 44; and a second cylindrical hole end section 45 which extends from the upper end of the intermediate hole section 20 to the upper end 17b of the guide member 17 and whose inner diameter is equal to or larger than the outer diameter of the trunk section 19 of the rod 44. The inner wall of the intermediate hole section 20 is provided with internal threads engageable with the external threads of the engagement section 22 to allow for the easy fitting of the rod 44 into the guide member 17. When the knob 16 is pressed for rotation to let the external threads of the engagement section 22 be fully engaged with the internal threads of the engagement hole 25, the trunk section 19 of the rod 44 is pressed against a shoulder 46 defined between the intermediate hole section 20 and second cylindrical hole section 45, thereby allowing the swing member 42 to be pressed against the upper surface 14a of the support 14 and the upper surface 3a of the base 3.

The depth or length of the second cylindrical hole section 45 is made several millimeters longer than that of the engagement section 22.

When, therefore, the rod 44 is fully pulled up, the engagement section 22 is completely released from the engagement hole 25 to be wholly inserted into the second cylindrical hole section 45, thereby allowing for the smooth rotation of the swing member 42 around the pivotal shaft 15. A compression coil spring 24 surrounding the rod 44 is disposed between the knob 16 and guide member 17 normally to elastically urge the rod 44 to be kept away from the swing member 42.

The surface 14a of the support 14 is provided with an abutment or projection 26. When the swing member 42 is set substantially at right angles to the electric flash tube 2 or base 3 (this position of the swing member 42 is hereinafter referred to as "the first position"), the abutment 26 prevents the swing member 42 from being further rotated toward the electric flash tube 2.

A mirror mount 27 carrying a reflection mirror 28 is set at the center of the upper surface of the swing member 42. The reflection mirror 28 has a light converging spherical or aspheric surface such as a spherical surface a parabolic surface. When the swing member 42 occupies the first position, causes the optical axis to be aligned with the optical axis X-X of the electric flash tube 2.

The mirror mount 27 comprises a first support member 29 formed of a square base section 29a disposed on the center of the surface of the swing member 42, and a pair of angle sections 29b projectively provided in both corners of that side of the base 29a which faces the electric flash tube 2; and a second support member 30 formed of a square base section 30a mounted on the base section 29a of the first support member 29 and a keep plate 30b which perpendicularly projects from the edge of that side of the square base 30a which faces the electric flash tube 2 and is spaced at a prescribed distance from that side of the angle section 29b of the first support member 29 which faces the electric flash tube 2.

The first and second support members 29, 30 are fixed onto the central part of the swing member 42 by means of suitable connecting means like screws 47 such that the optical axis of the reflection mirror 28 aligns with the optical axis X-X of the electric flash tube 2 when the mirror 28 is disposed between the support members 29, 30 and the swing member 42 is set in the first position. A space or opening 31 defined between the angle sections 29b of the first support member 29 is large enough to allow for the passage of said one end 2a of the electric flash tube 2, thereby enabling the reflection mirror 28 to be set very close to said one end 2a.

A light transmitting element 33 formed of, for example, an optical fiber bundle, and a converging lens 32 are provided near the other or forward end of the electric flash tube 2. Both light transmitting element 33 and converging lens 32 are mounted on the housing 4 in alignment with the optical axis X-X of the electric flash tube 2.

The converging lens 32 collects light rays directly sent forth from the electric flash tube 2 and light rays issued from the electric flash tube 2 and reflected by the reflection mirror 28 on the light receiving end 33a of the light transmitting element 33. Like the conventional type, the light transmitting element 33 used in this invention is connected to an illumination light transmitting element of an endoscope, thereby conducting light rays collected on the light receiving end 33a.

In operation, after the knob 16 of the swing member fixing means 43 of the reflection mirror retracting device 12 is rotated until the external threaded engagement section 22 is released from the internal threaded engagement hole 25 for the removal from or fitting to the rest 9 of the light source lamp 1, or for the replacement of the light source lamp 1, the rod 44 is pulled up by the urging force of the compression coil spring 24, thereby completely disengaging the engaging section 22 from the support 14. Later, as the knob 16 is moved along the optical axis X-X away from said one end or rear end 2a of the electric flash tube 2, the swing member 42 is horizontally rotated in the direction of an arrow A shown in FIG. 1 around the pivotal shaft 15 in parallel with the outer surface 4a of the housing 4, until the swing member 42 takes a position removed from said one end or rear end 2a of the electric flash tube 2 (this position is hereinafter referred to as "the second position"). As a result, the reflection mirror 28 is retracted from said one end or rear end 2a of the electric flash tube 2 and base 3 along with the mirror mount 27.

While the swing member 42 is set in the second position, the used light source lamp 1 is released from the light source lamp rest 9, or a new light source lamp 1 is fitted to the light source lamp rest 9. The above-mentioned release or fitting is carried out without any obstruction, because the reflection mirror-retracting device 12 is completely set apart from the electric flash tube 2.

When the fitting of a new light source lamp 1 is brought to an end, the knob 16 is moved in a direction opposite to that of the arrow A indicated in FIG. 1, thereby rotating the swing member 42 until it is pressed against the abutment or projection 26 to take the first position. Thereafter, the knob 16 is pressed down against the urging force of the compression coil spring 24, and further rotated to cause the externally threaded engagement section 22 to be fitted into the internally threaded engagement hole 25.

When the engagement section 22 is fully engaged with the engagement hole 25, the trunk section 19 of the rod 44 presses the shoulder 46 of the guide member 19, and consequently the underside of the swing member 42 presses the upper surface 3a of the base 3, thereby securely fitting the base 3 to the light source lamp rest 9. Therefore, the light source lamp 1 is held in a prescribed position relative to the light source lamp rest 9. To ensure the fitting of the light source lamp 1 in the prescribed position, it is possible to provide a stepped section 48 in that portion of the base 3 which lies adjacent to the hole 35 formed in the upper surface 3a of the base 3, thereby causing the facing edge of the swing member 42 to the tube 2 set in the first position to be pressed against the stepped section 48. When the swing member 42 is returned to the first position, the reflection mirror 28 is again set in the first position in which the reflection mirror 28 occupies a prescribed position adjacent to said one end or rear end 2a of the electric flash tube 2.

The foregoing embodiment comprised the externally threaded engagement member 22 and internally threaded engagement hole 25. However, it is possible to replace the engagement member 22 and engagement hole 25 with the thread-free types, substitute a tension coil spring for the compression coil spring 24, or omit this compression coil spring 24.

I claim:

1. A light source device which comprises:
   a housing having an outer surface;
   a light source lamp rest mounted on the outer surface of the housing;
   a light source lamp which has two ends and is detachably fitted to the light source lamp rest;
   a reflection mirror; and
   a reflection mirror-retracting mechanism which is set adjacent to one of said two ends of the light source lamp and which comprises a swing member carrying the reflection mirror, having two ends and swingable around one of said two ends of the swing member between a first position in which the reflection mirror is brought adjacent to said one end of the light source lamp and a second position in which the reflection mirror is retracted from the light source lamp, and fixing means for locking the swing member in the first position.

2. The light source device according to claim 1, wherein the reflection mirror-retracting mechanism comprises first and second supports which are mounted on the outer surface of the housing with said one end of the light source lamp disposed between the first and second supports, the first support rotatably supporting said one end of the swing member, and the second support being provided with the fixing means.

3. The light source device according to claim 2, wherein each of the first and second supports has an outer surface remote from, and parallel to the outer surface of the housing; and the first support is provided with a pivotal shaft which projects from the outer surface of the first support to rotatably support the swing member on the first support.

4. The light source device according to claim 3, wherein an engagement hole is formed in the outer surface of the second support; the other end of the swing member is provided with a penetrating hole aligned with the engagement hole when the swing member takes the first position; and the fixing means comprises a rod which is reciprocatively inserted into the penetrating hole and has two ends, one of which is engageable with the engagement hole.

5. The light source device according to claim 4, wherein said one end of the rod is provided with external threads; and the engagement hole is provided with internal threads engageable with the external threads of the rod.

6. The light source device according to claim 4, wherein the fixing means comprises a guide member which is fixed onto the swing member and provided with a guide hole which is aligned with the penetrating hole and through which the rod extends.

7. The light source device according to claim 6, wherein the guide hole comprises two end sections and an intermediate section; the two end sections have a larger inner diameter than the intermediate section; one of the two end sections communicates with the penetrating hole; the other of the two end sections is open to that side of the guide hole which lies remote from the penetrating hole; and the rod comprises an engagement section which is movable along the guide hole and the engagement hole and has a larger diameter than the intermediate section of the guide hole, a trunk section which is remote from the engagement hole and is inserted into the guide hole and has a larger diameter than the intermediate section of the guide hole, a sliding section which connects the engagement section with the trunk section and reciprocatively slides through the intermediate section of the guide hole, and an engagement section concentrically connected to the sliding section and forming said one end of the rod.

8. The light source device according to claim 7, wherein the engagement section of the rod is provided with external threads; and the engagement hole is provided with internal threads engageable with the external threads of the engagement section of the rod.

9. The light source device according to claim 7, wherein the guide member is provided with urging means for urging the rod in that direction in which the engagement section of the rod is released from the engagement hole.

10. The light source device according to claim 9, wherein the trunk section of the rod is provided with a knob; and the urging means is a compression coil spring stretched between the knob and guide member.

11. The light source device according to claim 10, wherein the engagement section of the rod is provided with external threads, and the engagement hole is provided with internal threads engageable with the external threads of the engagement section of the rod.

12. The light source device according to claim 11, wherein the second support is provided with an abutment for preventing the swing member from being rotated beyond the first position away from the second position.

* * * * *